United States Patent
Callas et al.

(10) Patent No.: US 7,276,075 B1
(45) Date of Patent: *Oct. 2, 2007

(54) ENDOSCOPIC SURGICAL ACCESS PORT AND METHOD

(75) Inventors: Peter Callas, Redwood City, CA (US); John P. Lunsford, San Carlos, CA (US); Albert K. Chin, Palo Alto, CA (US); Michael Wei, San Mateo, CA (US)

(73) Assignee: Origin Medsystems, Inc., Santa Clara, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/705,652

(22) Filed: Nov. 10, 2003

Related U.S. Application Data

(63) Continuation of application No. 09/648,660, filed on Aug. 25, 2000, now Pat. No. 6,811,546.

(51) Int. Cl.
*A61M 29/00* (2006.01)

(52) U.S. Cl. .................. 606/191; 606/192; 606/198

(58) Field of Classification Search ........ 606/190–194, 606/108, 1, 174, 185; 604/167.01–167.04, 604/167.06, 23–26, 174
See application file for complete search history.

(56) References Cited

U.S. PATENT DOCUMENTS

| | | | |
|---|---|---|---|
| 4,424,833 A | | 1/1984 | Spector et al. |
| 4,649,904 A | * | 3/1987 | Krauter et al. ............... 600/154 |
| 4,653,477 A | * | 3/1987 | Akui et al. .................. 600/154 |
| 4,685,447 A | | 8/1987 | Iversen et al. |
| 4,809,679 A | * | 3/1989 | Shimonaka et al. ........ 600/154 |
| 4,929,235 A | | 5/1990 | Merry et al. |
| 5,073,169 A | | 12/1991 | Raiken |
| 5,104,383 A | | 4/1992 | Shichman |
| 5,127,626 A | | 7/1992 | Hilal et al. |
| 5,167,636 A | | 12/1992 | Clement |
| 5,197,955 A | | 3/1993 | Stephens et al. |
| 5,226,891 A | | 7/1993 | Bushatz et al. |
| 5,263,939 A | | 11/1993 | Wortrich |
| 5,330,437 A | | 7/1994 | Durman |
| 5,354,280 A | | 10/1994 | Haber et al. |
| 5,366,446 A | | 11/1994 | Tal et al. |
| 5,437,646 A | | 8/1995 | Hunt et al. |
| 5,496,345 A | | 3/1996 | Kieturakis et al. |
| 5,545,179 A | * | 8/1996 | Williamson, IV ........... 606/213 |
| 5,607,397 A | | 3/1997 | Stephens et al. |
| 5,634,937 A | * | 6/1997 | Mollenauer et al. ........ 606/213 |

(Continued)

*Primary Examiner*—Michael J. Hayes
*Assistant Examiner*—Michael Mendoza
(74) *Attorney, Agent, or Firm*—Fenwick & West LLP

(57) ABSTRACT

A sliding gas-tight seal on an access port promotes insufflation of an anatomical space formed in tissue at a surgical site only during insertion of an endoscopic instrument through the access port into the anatomical space, and promotes deflation of the inflated space upon removal of the endoscopic instrument from within the access port. An inflatable balloon disposed about the port near the distal end may be selectively expanded to seal and anchor the access port within an incision through which a surgical procedure with insufflation is to be performed. Multiple resilient seals may be attached to the body of the port, and an auxiliary resilient seal may be inserted within the aperture of a seal attached to the body to accommodate a wide range of endoscopic instruments of various exterior dimensions inserted through the seals.

46 Claims, 2 Drawing Sheets

U.S. PATENT DOCUMENTS

| | | |
|---|---|---|
| 5,697,946 A | 12/1997 | Hopper et al. |
| 5,725,553 A | 3/1998 | Moenning |
| 5,836,913 A | 11/1998 | Orth et al. |
| 5,855,549 A | 1/1999 | Newman |
| 5,868,773 A | 2/1999 | Danks et al. |
| 5,871,471 A | 2/1999 | Ryan et al. |
| 5,873,889 A * | 2/1999 | Chin .......................... 606/190 |
| 5,979,452 A | 11/1999 | Fogarty et al. |
| 6,099,505 A | 8/2000 | Ryan et al. |
| 6,099,544 A | 8/2000 | Wolf et al. |
| 6,102,853 A | 8/2000 | Scirica et al. |
| 6,106,539 A | 8/2000 | Fortier |
| 6,110,154 A | 8/2000 | Shimomura et al. |
| 6,129,713 A | 10/2000 | Mangosong et al. |
| 6,142,955 A | 11/2000 | Farascioni et al. |
| 6,146,400 A | 11/2000 | Hahnen |
| 6,152,894 A | 11/2000 | Kubler |
| 6,162,196 A | 12/2000 | Hart et al. |
| 6,162,236 A | 12/2000 | Osada |
| 6,165,124 A | 12/2000 | Ouchi |
| 6,165,137 A | 12/2000 | Milliman et al. |
| 6,168,607 B1 | 1/2001 | Wattiez et al. |
| 6,187,002 B1 | 2/2001 | Long et al. |
| 6,189,533 B1 | 2/2001 | Simon et al. |
| 6,193,651 B1 | 2/2001 | DeFonzo |
| 6,197,041 B1 | 3/2001 | Shichman et al. |
| 6,200,263 B1 | 3/2001 | Person |
| 6,276,661 B1 | 8/2001 | Laird |
| 6,599,237 B1 | 7/2003 | Singh |
| 2001/0023332 A1 | 9/2001 | Hahnen |

* cited by examiner

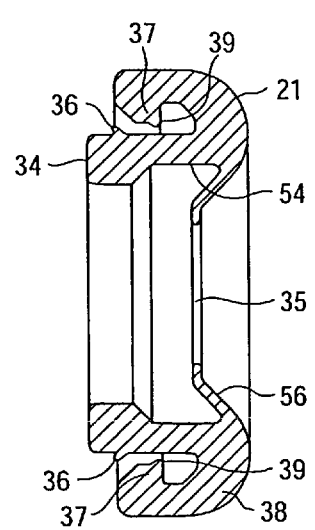
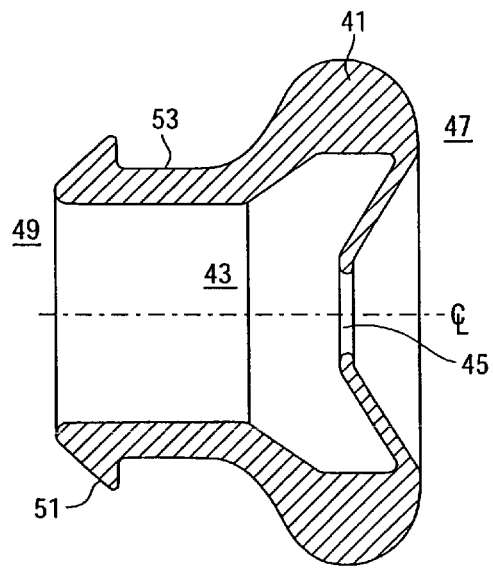
FIG. 5   FIG. 6
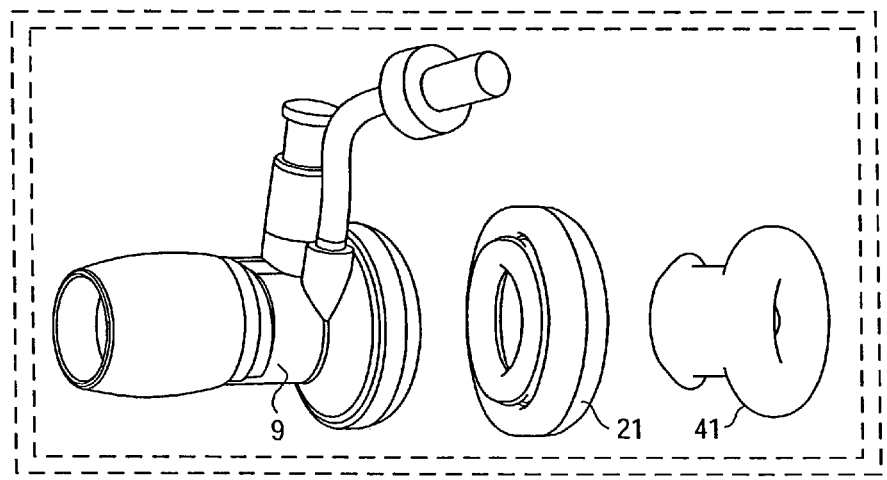
FIG. 7

US 7,276,075 B1

ENDOSCOPIC SURGICAL ACCESS PORT AND METHOD

RELATED APPLICATION

This application is a continuation of application Ser. No. 09/648,660, now U.S. Pat. No. 6,811,546, entitled "Endoscopic Surginal Access Port and Method", filed on Aug. 25, 2000 by Peter Callas, et al.

FIELD OF THE INVENTION

This invention relates to endoscopic surgical apparatus and methods of tissue dissection, and more particularly to a sliding gas seal for controlling insufflation of an endoscopic surgical site on a patient.

BACKGROUND OF THE INVENTION

Coronary bypass surgery commonly requires a length of the saphenous vein of the patient to form a shunting vessel around a site of stenosis or other blockage in a coronary artery. The saphenous vein was conventionally 'harvested' from the patient's leg through an incision extending the length of the section of saphenous vein to be harvested. Recently, endoscopic surgical procedures have replaced open-incision harvesting procedures and have significantly reduced patient trauma, discomfort, complication and recovery time. Specifically, contemporary vein-harvesting procedures require only a small incision over the saphenous vein to expose the vein, and then blunt tissue dissection is performed along the length of the vein using an elongated endoscopic cannula inserted through the incision to detach the vein and lateral branch vessels from connective tissue along the length of the vein to be harvested. The channel or anatomical space thus formed within the bluntly dissected tissue along the course of the vessel may be expanded to provide additional space within which to perform associated surgical procedures such as clipping and ligating lateral branch vessels using mechanical retractors inserted within the channel to elevate tissue away from the vein being harvested.

Alternatively, the channel or anatomical space formed along the course of the vessel may be retained in expanded condition by insufflating the channel with gas under pressure. The gas may be supplied through an access port which admits endoscopic instruments through a sliding gas-tight seal that is inserted into and sealed within the small initial incision over the saphenous vein. Conventional access ports commonly include a hollow body with an expandable peripheral balloon disposed about the outer distal end of the body, and with one or more diaphragm-type sliding seals disposed at the proximal end across the central bore of the hollow body. In operation, such conventional access port is inserted into a small incision and the peripheral balloon is then inflated to seal the port within the incision. Gas under pressure may then be supplied through the access port as elongated endoscopic instruments are inserted, and manipulated through the sliding seal during surgical procedures within the anatomical space formed along the vein, without significant loss of gas pressure within the anatomical space during insertions and removals of surgical instruments through the sliding seal of the access port. For convenience, the hollow body may include multiple sliding gas seals that are selectively positioned on the proximal end of the port to accommodate a selection of elongated instruments of different diameters passing through the central bore of the hollow body. Such access ports include a flapper valve to inhibit outflow of gas therethrough as an elongated instrument is withdrawn from the central bore. However, the versatility of selectable seals and flapper valves to accommodate endoscopic instruments of various diameters significantly extends the length of the hollow body and requires additional manual re-configuration to position a selected seal over the proximal end of the hollow body to provide a sliding seal of appropriate dimensions to accommodate the diameter of a selected endoscopic instrument.

SUMMARY OF THE INVENTION

In accordance with embodiments of the apparatus and method of the present invention, an access port is provided which obviates the need for flapper valves and selectable sliding seals that snap toggle into position over the proximal end of the hollow body. This facilitates insufflation of an anatomical space during the interval while an endoscopic instrument is positioned through the hollow body. In recognition of the typically small spatial volume of a channel or anatomical space formed along the saphenous vein, it has been discovered that insufflation need only be established during insertion and manipulation of an endoscopic instrument through the access port, and that re-pressurization of the small volume can be satisfactorily restored within a very brief interval following insertion of an endoscopic instrument through the sliding seal of the access port.

BRIEF DESCRIPTION OF THE DRAWINGS

FIG. 5 is a sectional view of one sliding gas seal for engagement on the proximal end of the body of FIG. 3;

FIG. 6 is a sectional view of a sliding gas seal for assembly on the embodiment of FIG. 1; and FIG. 7 is a perspective view of an access port kit according to the present invention.

DETAILED DESCRIPTION OF THE INVENTION

Figure 1:
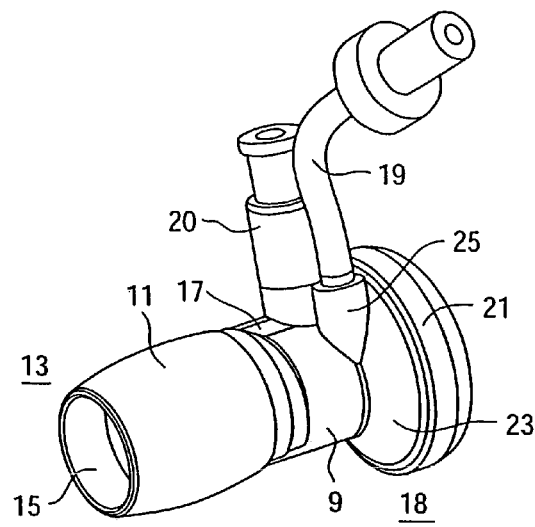
FIG. 1 is perspective view of an access port in accordance with one embodiment of the present invention.
Figure 2:
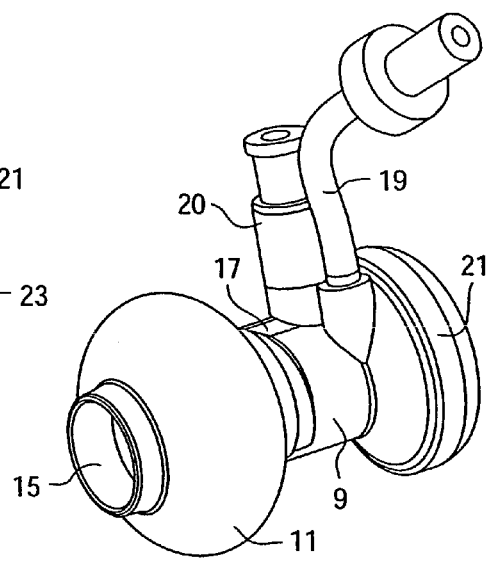
FIG. 2 is a perspective view of the access port of FIG. 1 with the incision-sealing balloon inflated.

Referring now to FIG. 1, there is shown a perspective view of the access port according to one embodiment of the present invention in which the hollow body 9 of fluid-impervious material includes a central bore 15 and a generally toroidally-shaped balloon 11 disposed about the outer periphery of the body 9 near the distal end 13 thereof. The interior diameter of the central bore 15 through the hollow body 9 is sized to accommodate the largest diameter of endoscopic instrument therein and may be about 0.6" at the distal end 13, and may flair out to a wider diameter of about 0.9" at the proximal end 18. A fluid or air passage 17 along an outer wall of the body 9 connects to an external fluid-tight fitting 20 for coupling to a source of gas under pressure, such as a syringe, in order to selectively inflate the balloon 11 within the confines of an initial cutaneous incision near a saphenous vein that is to be harvested. Inflating the balloon 11 with fluid under pressure, as shown in FIG. 2, seals and mechanically anchors the body 9 within an incision to serve as the access port for endoscopic instruments thereafter inserted through the central bore 15 of the hollow body 9 into the incision.

Figure 3:
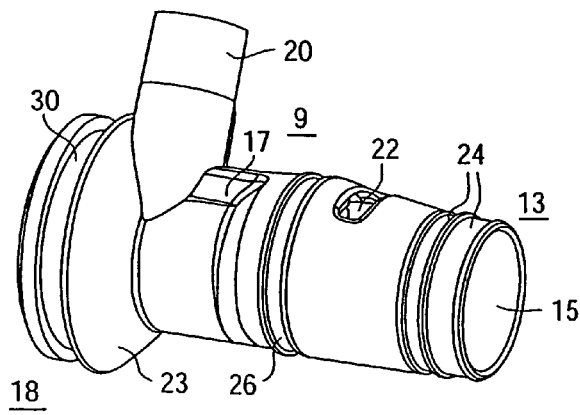
FIG. 3 is a perspective view of the body of the access port of FIG. 1 as a molded component.

Referring now to FIG. 3, there is shown a perspective view of the body 9 as a molded component formed, for example, of bioinert material such as polycarbonate. Specifically, the body 9 includes an integral air passage 17 communicating with the gas fitting 20 and the aperture 22 (within the volume confined by the balloon 11, not shown). This integral air passage thus facilitate selective inflation of the balloon 11 via a pressure fitting 20. Alternatively, the fitting 20 may include a one-way valve to retain inflation of the balloon until such valve is selectively released. The balloon 11 is attached to the body 9 within the circumferential groove, or grooves, 24 near the outer perimeter of the distal end 13, and is also attached to the circumferential groove 26 about the outer perimeter of the body 9 at a location thereon intermediate the distal end 13 and proximal end 18. The integral air passage 17 extends the outer dimension of the body 9 between the pressure fitting 20 and the aperture 22, so groove 26 may be elliptical in the plane normal to the axis of the central bore 15. A balloon 11 thus attached to the body 9, as described above, may inflate in substantially toroidal configuration, as illustrated in FIG. 2, with an elliptical shape disposed within groove 26 and a substantially circular shape disposed within groove 24.

Figure 4:
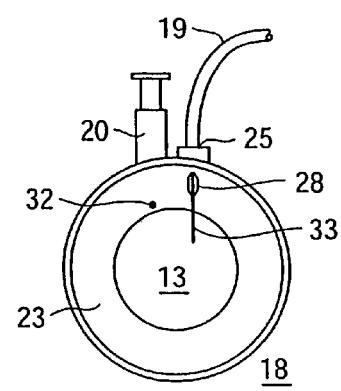
FIG. 4 is a proximal end view of the body of FIG. 3.

At the proximal end 18 of the body 9, the central bore 15 flairs out to a larger diameter over a short transition section 23 that provides an internal wall which tapers between the larger and smaller diameter segments of the central bore 15. The outer perimeter of the proximal end 18 of the body 9 includes a recessed groove 30 that accommodates gas-tight attachment of a resilient seal, later described herein. The expanded diameter of the central bore 15 near the proximal end 18 of the body 9 accommodates a wide range of angulation of an endoscopic instrument within the central bore 15 without interference from the side walls of the internal bore. Also, as shown in the proximal end view of FIG. 4, an insufflation gas inlet 25 is formed on the transition section 23, with an internal aperture 28 positioned in the tapering internal wall of the transition section 23. This assures that insufflating gas or other fluid supplied through the conduit 19 and the aperture 28 will not be blocked or restricted by an endoscopic instrument of largest diameter inserted within the central bore 15. In another embodiment of the present invention, the conduit 19 for insufflating gas or other fluid under pressure may be normally sealed off, for example, via a resiliently-biased disk against a downstream valve seat, with a control arm 33 rigidly attached centrally on the disk and protruding through the aperture 28 into the central bore 15 to open the valve in response to an endoscopic instrument inserted in central bore 15 to displace the control arm 33. Molding of the body 9 with an air passage between the pressure fitting 20 and the aperture 22 (for inflating the balloon 11) is greatly facilitated by a pin-like mandrel disposed away from, but aligned with, the central bore 15 and emanating through the internal tapered wall of the transition section 23. Such pin-like mandrel intersects with another mandrel that forms the internal bore through the pressure fitting 20 to provide the integrally-molded air passage 17 between fitting 20 and aperture 22, with a remnant aperture 32 remaining in the internal tapered wall where the pin-like molding mandrel was withdrawn. This aperture 32 may be permanently plugged with a drop of glue or sealant, or the like, to provide a gas-tight air passage between fitting 20 and the aperture 22. Alternatively, a tube as an insert may be molded into the body 9 to form the air passage between fitting 20 and aperture 22, without an aperture 32 formed during such molding procedure.

In another embodiment, the body 9 and the sliding seal 21 may be integrally formed as a single molding of a bioinert material such as silicone rubber. In such embodiment, the more rigid section of the body 9 includes thicker walls and the more flexible section of the seal 21 includes thinner walls, with other components, features and configuration (except a grove 30) formed as previously described herein.

Referring now to FIG. 5, there is shown a sectional view of a generally round sliding-seal component 21 for gas-tight attachment to the generally cylindrical proximal end 18 of the body 9. The seal 21 is formed of resilient, flexible polymeric material to include a central aperture 35. The aperture 35 overlays and aligns with the central bore 15 at the proximal end of the hollow body. The aperture 35 has a smaller diameter than the largest endoscopic instrument to be inserted through the hollow body 9. A sliding gas-tight seal is thus formed about the outer generally cylindrical surface of an endoscopic instrument during insertion thereof through the hollow body 9. The outer perimeter of the gas seal component 21 is configured to overlap the proximal end 18 of the body 9 and resiliently snap into groove 30 for gas-tight and mechanically-secure attachment to the body 9. Specifically, the distal end 34 is configured to insert within the internal walls of the proximal end 18 of the body 9, and includes an integrally-formed raised ring 36 on such outer diameter to provide a deformable gas-tight seal between the gas seal component 21 and the internal walls of the body 9. In addition, the overlapping flange 38 at the proximal end of the gas seal component 21 includes a descending and inwardly extending portion 37 that is integrally formed on the gas seal component to engage within the groove 30 in the outer perimeter near the proximal end of the body 9. In addition, the inwardly extending portion includes an integrally-formed inwardly extending ring 39 that provides a deformable gas seal within the groove 30 in body 9. The gas-sealing component 21 thus configured forms gas-tight seals about the proximal end 18 of the body 9, and forms a sliding gas-tight seal about an endoscopic instrument inserted through the aperture 35. The entry port 28 into the hollow body 9 is positioned interior of sliding seal 21 for supplying gas under pressure via gas line 19 to an anatomical space into which the access port is inserted. Thus, with the body 9 sealed and anchored within an incision by the inflated balloon 11, and with an endoscopic instrument inserted through the sliding seal 21 and hollow body 9, an anatomical space of confined volume is formed about a saphenous vein to be harvested which can be insufflated with gas under pressure supplied to the confined volume through the fluid conduit 19 and entry port 28. As the endoscopic instrument is removed from the access port, the fluid seal around the endoscope is disabled, and air or other fluid under pressure within the confined volume about the saphenous vein equalizes rapidly toward ambient pressure. Only after an endoscopic instrument is again inserted within the central bore of the hollow body 9 is the fluid seal re-formed at aperture 35, and the confined volume about the saphenous vein re-insufflated with gas or other fluid under pressure that may be continuously supplied via the gas entry port 28.

For operation with an endoscopic instrument of smaller exterior diameter than would form a seal within aperture 35, sliding auxiliary gas seal 41 may be formed in the configuration as illustrated in FIG. 6 for insertion into the aperture 35 of seal 21. The auxiliary seal 41 is substantially circularly toroidal with an internal bore 43 of larger diameter than the diameter of the sealing aperture 45 at the proximal end 47.

A tapered and outwardly extending hook-like ring 51 is integrally formed on the distal end 49 of the auxiliary seal 41 at a distance from the proximal end 47 suitable for engaging the inner surface 54 behind the diaphragm member 56. Alternatively, the ring 51 may be integrally formed on the distal end 49 of the auxiliary seal 41 at a distance from the proximal end 47 suitable for engaging the distal end 34 of the seal 21. The outer diameter 53 is disposed to fit within the inner diameter of seal 21 at the distal end thereof. In this way, the auxiliary seal 41 may form a gas-tight and mechanically-stable auxiliary seal about endoscopic instruments of smaller diameter suitable for forming a sliding seal within aperture 45. The toroidally-shaped seals 21, 41 may be formed of a flexible, resilient material such as polyurethane, silicone, latex rubber, Nitrile, or the like, to exhibit resilient flexibility upon installation of seal 21 over the proximal end 18 of the body 9, and upon optional installation of the auxiliary seal 41 within the aperture 35 of seal 21. A seal 21 formed and assembled in this manner on the body 9 with optional auxiliary seal 41 inserted in seal 21, significantly reduces the length and mass and associated cost of an access port suitable for accommodating large-diameter and small-diameter endoscopic instruments while also supporting insufflation of a surgical site, such as along a saphenous vein, of relatively small confined volume. In addition, the short length of body 9 greatly extends the range of angulation of an endoscopic instrument within the central bore 15 without adversely altering the position of the body 9 sealed within an incision. And, the inner walls of the resilient seal 21 and auxiliary seal 41 serve as bumpers to limit angular and lateral movement of an endoscopic instrument and prevent distortion of the associated aperture in response to excessive angular movement. The balloon inflation port 20 and the insufflation gas port 19, 25 may also be oriented in substantial axial alignment, rather than in lateral alignment, with the central bore 15 to increase the range of angular orientations of the body 9 within an incision. Axial configuration of the gas ports in another embodiment of the present invention facilitates reduced size of the body and insertion thereof into an incision with the seal 21 oriented distally and the balloon 11 oriented proximally. And, an eccentric mounting of the balloon on the body at a location thereon intermediate the distal and proximate ends promotes wider angles of orientation of the central bore relative to an incision formed above a saphenous vein to be harvested. The body with attached balloon and one or more resilient seals having apertures of various diameters, and including an auxiliary seal for fluid-tight insertion into the aperture of a resilient seal that attaches to the proximal end of the body, may all be assembled in pre-sterilized condition within a hermetically-sealed conventional tray pack or pillow pack, as illustrated in FIG. 7, to facilitate forming an insufflation access port with sliding seals about endoscopic instruments of various exterior dimensions.

What is claimed is:

1. Fluid sealing apparatus for operation with an endoscopic instrument at a surgical site, the apparatus comprising:
   a body having a central bore dimensioned to receive an endoscopic instrument therein, the bore extending through the body between distal and proximal ends thereof;
   an element disposed about the body near one of the distal and proximal ends thereof for selectively expanding radially outwardly about the body to provide an external tissue seal; and
   a fluid seal disposed about the body near the other of the distal and proximal ends having an aperture therethrough substantially aligned with the central bore through the body, and having an inner dimension resiliently and flexibly disposed to receive an endoscopic instrument therein in sliding fluid-sealing engagement therewith, wherein the diameter of the central bore is large enough to permit a range of angulation of an endoscopic instrument extending through the central bore,
   wherein the body includes a plurality of circumferential grooves for receiving and retaining both the element and the fluid seal.

2. The apparatus according to claim 1 in which the element includes a balloon of substantially toroidal-shape attached to an outer surface of the body near the distal end thereof, and comprising:
   a fluid passage in a wall of the body in communication with the balloon and extending along the wall toward the proximal end of the body for connection thereat to a source of fluid under pressure for selectively inflating the balloon.

3. The apparatus according to claim 1 in which the fluid seal includes a generally toroidally-shaped member removably attached in fluid-sealing engagement with the proximal end of the body.

4. Fluid sealing apparatus according to claim 3 including an inlet conduit communicating with the bore intermediate the attachment of the member with the proximal end of the body, and the distal end thereof.

5. Fluid sealing apparatus according to claim 1 including an inlet conduit communicating with the bore for supplying fluid under pressure thereto.

6. Fluid sealing apparatus according to claim 5 including a valve disposed within the inlet conduit for selectively controlling flow of fluid under pressure therethrough, the valve including an actuator attached thereto for configuring the valve to permit fluid under pressure to flow therethrough in response to engagement of the actuator with an endoscopic instrument disposed within the bore.

7. Fluid sealing apparatus according to claim 5 in which the central bore includes a portion thereof of diverging sectional dimension toward the proximal end thereof; and
   the inlet conduit communicates with the portion of diverging sectional dimension.

8. Fluid sealing apparatus according to claim 6 in which the actuator includes a lever protruding through the inlet conduit to configure the valve for fluid now therethrough in response to engagement of the lever with an endoscopic instrument disposed within the bore.

9. The apparatus according to claim 1 wherein the element comprises a balloon, and wherein a pair of grooves provided at the distal end of the body is sized and spaced to retain the balloon on the exterior of the body, the body including a fluid passage in a wall thereof that opens outwardly at a location on the body between the two grooves in the pair of grooves.

10. The apparatus according to claim 1 wherein the resilient fluid seal is disposed at the proximal end of the body and defines a transition section flared outward in a proximal direction.

11. The apparatus according to claim 10 wherein the body includes an insufflation gas inlet having an aperture opening into the central bore at the transition section.

12. The apparatus according to claim 10 wherein the central bore is at least 0.6 inches in diameter.

13. The apparatus according to claim 1 wherein the proximal end of the central bore defines a transition section flared outward in a proximal direction to increase the diameter of the central bore by at least about 50% from the distal end thereof.

14. An endoscopic surgical procedure performed through an access port, the procedure comprising:
forming an incision in tissue;
dissecting tissue to form an anatomical space in tissue in communication with the incision;
inserting the access port within the incision and anatomical space;
laterally outwardly expanding the portion of the access port inserted within the incision to form fluid-sealing engagement with tissue about the incision;
inserting an endoscopic instrument into the anatomical space through the access port;
forming a fluid-tight seal in the access port in response to insertion of the endoscopic instrument in the access port;
insufflating the anatomical space with fluid under pressure during formation of the fluid-tight seal; and
disabling a fluid-tight seal within the access port to permit deflating the anatomical space inflated with fluid under pressure upon removal of an endoscopic instrument from within the access port.

15. The endoscopic surgical procedure according to claim 14 in which insufflating the anatomical space is performed with fluid under pressure supplied through the access port.

16. The endoscopic surgical procedure according to claim 15 in which supply of fluid under pressure is terminated in response to removal of an endoscopic instrument from within the fluid-tight seal in the access port.

17. The endoscopic surgical procedure according to claim 14 wherein the portion of the access port inserted within the incision includes a balloon, and wherein the step of laterally outwardly expanding comprises inflating the balloon.

18. The endoscopic surgical procedure according to claim 14 wherein the access port is defined by a body and a central bore therethrough, wherein the diameter of the central bore is large enough to permit a range of angulation of an endoscopic instrument extending therethrough.

19. The endoscopic surgical procedure according to claim 14 wherein the access port is defined by a body and a central bore therethrough and a primary resilient fluid seat attached to a proximal end thereof, wherein the step of forming a fluid-tight seal in the access port is accomplished by contact between an inner aperture of the primary resilient fluid seal and the endoscopic instrument.

20. The endoscopic surgical procedure according to claim 19 further including attaching an auxiliary resilient fluid seal to the primary resilient fluid seal, the auxiliary resilient fluid seal having an inner aperture smaller than the inner aperture of the primary resilient fluid seal.

21. An access port kit including:
a body having a central bore therethrough between distal and proximal ends thereof;
an element disposed about the body near the distal end thereof for selectively expanding laterally outwardly from the body;
a plurality of resilient fluid seals, each selectively attachable to the proximal end of the body for forming a fluid-tight seal with the body near the proximal end thereof, each of the fluid seals including a resilient aperture therethrough of selected different dimensions disposed to axially align with the central bore in the body in position attached to the proximal end of the body.

22. An access port kit according to claim 21 in which the body includes an inlet conduit communicating with the central bore for supplying fluid under pressure thereto at a location therein intermediate attachment of a fluid seal to the body and the distal end thereof.

23. An access port kit according to claim 22 including a valve disposed within the inlet conduit for selectively controlling flow therethrough of fluid under pressure in response to insertion of an endoscopic instrument within the resilient aperture of a fluid seal.

24. An access port kit according to claim 21 wherein the plurality of resilient fluid seals comprises a generally annular primary fluid seal including an outer perimeter adapted to couple to the proximal end of the body and having a resilient aperture being defined by a diaphragm extending inwardly from the outer perimeter and formed of a portion of the polymeric material that is thinner-walled than the outer perimeter.

25. An access port kit according to claim 24 wherein the body includes a plurality of circumferential grooves for receiving and retaining the primary resilient fluid seal.

26. An access port kit according to claim 24 wherein the plurality of resilient fluid seals further includes an auxiliary resilient fluid seal attachable to the primary resilient fluid seal and having an aperture defined by an inwardly extending diaphragm that is smaller than the aperture in the primary resilient fluid seal.

27. An access port kit according to claim 21 wherein the element comprises a balloon, and wherein the body includes a pair of grooves provided at its distal end sized and spaced to retain the balloon on the exterior of the body, the body including a fluid passage in a wall thereof that opens outwardly at a location on the body between the two grooves in the pair of grooves.

28. An access port kit according to claim 27 further including a fitting leading to the fluid passage and a one-way valve associated therewith to maintain inflation of the balloon.

29. An access port kit including:
a body having a central bore therethrough between distal and proximal ends thereof;
an element disposed about the body near the distal end thereof for selectively expanding laterally outwardly from the body;
at least one resilient fluid seal for attachment in fluid-tight engagement with the body near the proximal end thereof, and including a resilient aperture therethrough of selected dimension to axially align with the central bore upon attachment to the body; and
an auxiliary resilient fluid seal for insertion within the resilient aperture of the resilient fluid seal to form a fluid-tight seal therewith, including an aperture therein of smaller dimension than the resilient aperture of the resilient fluid seal for forming a sliding, substantially fluid-tight seal about a cylindrical member of sectional dimension larger than the aperture in the auxiliary resilient fluid seal and smaller than the aperture in the resilient fluid seal.

30. An access port kit according to claim 29 wherein the body includes a plurality of circumferential grooves for receiving and retaining the resilient fluid seal.

31. An access port kit according to claim 29 wherein the element comprises a balloon, and wherein the body includes a pair of grooves provided at its distal end sized and spaced to retain the balloon on the exterior of the body, the body including a fluid passage in a wall thereof that opens outwardly at a location on the body between the two grooves in the pair of grooves.

32. An access port kit according to claim 31 further including a fitting leading to the fluid passage and a one-way valve associated therewith to maintain inflation of the balloon.

33. Fluid sealing apparatus for operation with an endoscopic instrument at a surgical site, the apparatus comprising:
a body having a central bore dimensioned to receive an endoscopic instrument therein, the bore extending through the body between distal and proximal ends thereof;
an inflatable element disposed about the body near one of the distal and proximal ends thereof for selectively expanding radially outwardly about the body unobstructively of the central bore;
a resilient fluid seal disposed external to the body near the other of the distal and proximal ends having an aperture therethrough substantially aligned with the central bore through the body, and having an inner dimension resiliently and flexibly disposed to receive an endoscopic instrument therein in sliding fluid-sealing engagement therewith;
an inlet conduit communicating with the bore for supplying fluid under pressure thereto; and
a valve disposed within the inlet conduit for selectively controlling flow of fluid under pressure therethrough, the valve including an actuator attached thereto for configuring the valve to permit fluid under pressure to flow therethrough in response to engagement of the actuator with an endoscopic instrument disposed within the bore.

34. An access port kit including:
a body having a central bore therethrough between distal and proximal ends thereof;
an element disposed about the body near the distal end thereof for selectively expanding laterally outwardly from the body;
a plurality of resilient fluid seals, each selectively attachable to the proximal end of the body for forming a fluid-tight seal with the body near the proximal end thereof, each of the fluid seals including a resilient aperture therethrough of selected different dimensions disposed to axially align with the central bore in the body in position attached to the proximal end of the body; and
wherein the body includes an inlet conduit communicating with the central bore for supplying fluid under pressure thereto at a location therein intermediate attachment of a fluid seal to the body and the distal end thereof, and further including a valve disposed within the inlet conduit for selectively controlling flow therethrough of fluid under pressure in response to insertion of an endoscopic instrument within the resilient aperture of a fluid seal.

35. Fluid seating apparatus for operation with an endoscopic instrument at a surgical site, the apparatus comprising:
a body having a central bore dimensioned to receive an endoscopic instrument therein the bore extending through the body between distal and proximal ends thereof;
an element disposed about the body near one of the distal and proximal ends thereof for selectively expanding radially outwardly about the body to provide an external tissue seal; and
a fluid seal disposed about the body near the other of the distal and proximal ends having an aperture therethrough substantially aligned with the central bore through the body, and having an inner dimension resiliently and flexibly disposed to receive an endoscopic instrument therein in sliding fluid-sealing engagement therewith, wherein the diameter of the central bore is large enough to permit a range of angulation of an endoscopic instrument extending through the central bore, and
wherein the fluid seal is generally annular and comprised of a resilient polymeric material the fluid seal including an outer perimeter adapted to couple to the other of the distal and proximal ends of the body, and the aperture being defined by a diaphragm extending inwardly from the outer perimeter and formed of a portion of the polymeric material that is thinner-walled than the outer perimeter for providing an effective fluid-seal around an endoscope received therein.

36. The apparatus according to claim 35 in which the element includes a balloon of substantially toroidal-shape attached to an outer surface of the body near the distal end thereof, and comprising:
a fluid passage in a wall of the body in communication with the balloon and extending along the wall toward the proximal end of the body for connection thereat to a source of fluid under pressure for selectively inflating the balloon.

37. The apparatus according to claim 35 in which the fluid seal includes a generally toroidally-shaped member removably attached in fluid-sealing engagement with the proximal end of the body.

38. Fluid sealing apparatus according to claim 37 including an inlet conduit communicating with the bore intermediate the attachment of the member with the proximal end of the body, and the distal end thereof.

39. Fluid sealing apparatus according to claim 35, including an inlet conduit communicating with the bore for supplying fluid under pressure thereto.

40. Fluid sealing apparatus according to claim 39 in which the central bore includes a portion thereof of diverging sectional dimension toward the proximal end thereof; and
the inlet conduit communicates with the portion of diverging sectional dimension.

41. Fluid sealing apparatus according to claim 39 including a valve disposed within the inlet conduit for selectively controlling flow of fluid under pressure therethrough, the valve including an actuator attached thereto for configuring the valve to permit fluid under pressure to flow therethrough in response to engagement of the actuator with an endoscopic instrument disposed within the bore.

42. Fluid sealing apparatus according to claim 41 in which the actuator includes a lever protruding through the inlet conduit to configure the valve for fluid flow therethrough in response to engagement of the lever with an endoscopic instrument disposed within the bore.

43. The apparatus according to claim 35 wherein the resilient fluid seal is disposed at the proximal end of the body and defines a transition section flared outward in a proximal direction.

44. The apparatus according to claim 43 wherein the body includes an insufflation gas inlet having an aperture opening into the central bore at the transition section.

45. The apparatus according to claim 43 wherein the central bore is at least 0.6 inches in diameter.

46. The apparatus according to claim 35 wherein the proximal end of the central bore defines a transition section flared outward in a proximal direction to increase the diameter of the central bore by at least about 50% from the distal end thereof.

* * * * *